(12) United States Patent
Mills et al.

(10) Patent No.: US 8,071,507 B2
(45) Date of Patent: Dec. 6, 2011

(54) PLANT GROWTH REGULATING AND FUNGICIDAL COMPOSITIONS

(75) Inventors: Colin Edward Mills, Basel (CH); Ulrich Johannes Haas, Stein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 530 days.

(21) Appl. No.: 12/096,915

(22) PCT Filed: Dec. 11, 2006

(86) PCT No.: PCT/EP2006/011889
§ 371 (c)(1),
(2), (4) Date: Sep. 30, 2008

(87) PCT Pub. No.: WO2007/068421
PCT Pub. Date: Jun. 21, 2007

(65) Prior Publication Data
US 2009/0305893 A1    Dec. 10, 2009

(30) Foreign Application Priority Data

Dec. 13, 2005 (EP) .................................. 05027160

(51) Int. Cl.
*A01N 43/00* (2006.01)
*A01N 43/647* (2006.01)
(52) U.S. Cl. ........................ 504/139; 514/383
(58) Field of Classification Search ................. 504/139; 514/383
See application file for complete search history.

(56) References Cited

FOREIGN PATENT DOCUMENTS

| EP | 0088256 | 9/1983 |
| EP | 1304038 | 4/2003 |

OTHER PUBLICATIONS

Gilley, A., Relative Efficacy of Paclobutrazol, Propiconazole, and Tetraconazole as Stress Protectants in Wheat Seedlings, 1997 Plant Growth Regulation, vol. 21, pp. 169-175.*
Eureka Final Report Summary, Fungicide Strategies in Integrated management of Wheat and Barley Leaf Diseases in Southern WA [online]. Grains Research and Development Corporation, 2002 [retrieved on Nov. 9, 2010]. Retrieved from the Internet:<http://www.grdc.com.au/GRDC/ResearchSummaries/CMAttachments/daw589.pdf> pp. 1-3.*
Beckett, R.P., The Effect of Thidiazuron on the Yield of Wheat Grown with Varying Nutrient Supply, 1992, Plant Growth Regulation, vol. 11, pp. 343-348.*
Database CA [Online] Chemical Abstracts Service, Columbus, Ohio, US; T.J. Banko: "Potential additive growth regulator effects of triazole fungicides on bedding plants treated with growth regulators" XP002484575, retrieved from STN-International Database accession No. 144:46506 abstract & Proceedings—Plant Growth Regulation Society of America (2004), 31ST, 2004, pp. 100-103.
Database CAB [Online] CAB International, Wallingford Oxon, GB; J.G. Hampton et al.: "Seed yield response to fungicide application in paclobutrazol treated perennial ryegrass"; XP002484576, retrieved from STN-International Database accession No. 88:91060 abstract; Journal of Applied Seed Production, vol. 3, 1985, pp. 11-14.
Databasae CAB—[Online], CAB International, Wallingford, Oxonn, GB; S.W. Lee et al: "Growth control in 'New Guinea' impatiens (Impatiens hawkeri hybrids) by treatments of plant growth retardants and triazole fungicides;" XP002484577, retriEved from STN-International, Database accession No. 2001:65487 abstract & Korean Journal of Horticultural Science & Technology, vol. 18, No. 6, 2000, pp. 827-833.
Database Biosis [Online] Biosciences Information Service, Philadelphia, PA, US; Aug. 1999, Mercier Julien: "Use of growth regulator paclobutrazol in the management of dollar spot of creeping bentgrass in Minnesota", XP002484578, Database accession No. PREV200000272591 abstract, & Phytoprotection, vol. 80, No. 2, Aug. 1999, pp. 65-70. ISSN: 0031-9511.

* cited by examiner

*Primary Examiner* — Johann Richter
*Assistant Examiner* — Andriae M Holt
(74) *Attorney, Agent, or Firm* — Rebecca Howard

(57) ABSTRACT

The present invention provides a composition capable of regulating growth of a plant or propagation material thereof comprising as plant growth regulating active ingredient a mixture of component (A) and component (B) wherein component (A) is Paclobutrazole and component (B) is selected from the group consisting of Difenoconazole, Ipconazole, Metconazole, Tebuconazole, Prothioconazole, Cyproconazole, Propiconazole and Epoxiconazole wherein component (A) and component (B) are present in said composition in amounts which produce a synergistic effect. Preferably the composition comprises Paclobutrazole and Difenoconazole and the composition inhibits growth of the plant upon application thereby increasing yield/quality. The compositions are also capable of preventing and/or treating growth and/or infestation of phytopathogenic fungion a plant or propagation material thereof.

17 Claims, No Drawings

PLANT GROWTH REGULATING AND FUNGICIDAL COMPOSITIONS

This application is a 371 of International Application No. PCT/EP2006/011889 filed Dec. 11, 2006, which claims priority to EP 05027160.0 filed Dec. 13, 2005, the contents of which are incorporated herein by reference.

The present invention relates to novel compositions for regulating plant growth and for controlling phytopathogenic fungi. It further relates to the use of said compositions for regulating plant growth, in particular inhibiting plant growth to increase yield and for the control of phytopathogenic fungi.

Paclobutrazol ((2RS,3RS)-1-(4-chlorophenyl)-4,4-dimethyl-2-(1H-1,2,4-triazol-1-yl)-pentan-3-ol) is a plant growth regulator. It is used to produce more compact and mechanical resisting plants. It is, therefore, used to reduce lodging and increase yield in useful plants.

Examples of other known plant growth regulators include Prohexadione (3,5-dioxo-4-(1-oxopropyl)cyclohexanecarboxylate) and Chlormequat (2-chloro-N,N,N-trimethylethanaminium).

Triazole fungicides, including Difenoconazole (1-[2-[2-chloro-4-(4-chlorophenoxy)phenyl]-4-methyl-1,3-dioxolan-2-ylmethyl]-1H-1,2,4-triazole), are steroid demethylation inhibitors (ergosterol biosynthesis inhibitors) and are used as fungicides which are effective against a number of diseases caused by Ascomycetes, Basidiomycetes and Deuteromycetes.

It has now been found, surprisingly, that the plant growth regulating property of Paclobutrazol and some other plant growth regulating compounds can be significantly enhanced when combined with a triazole fungicide selected from Difenoconazole, Ipconazole, Metconazole, Tebuconazole, Prothioconazole, Cyproconazole, Propiconazole and Epoxiconazole.

Accordingly the present invention provides a composition capable of regulating growth of a plant or propagation material thereof comprising as plant growth regulating active ingredient a mixture of component (A) and component (B) wherein component (A) is Paclobutrazole and component (B) is selected from the group consisting of Difenoconazole, Ipconazole, Metconazole, Tebuconazole. Prothioconazole, Cyproconazole, Propiconazole and Epoxiconazole wherein component (A) and component (B) are present in said composition in amounts which produce a synergistic effect.

The present invention still further provides a composition capable of controlling phytopathogenic fungi on a plant or propagation material thereof comprising as fungicidal active ingredient a mixture of component (A) and component (B) wherein component (A) is Paclobutrazole and component (B) is selected from the group consisting of Difenoconazole, Ipconazole, Metconazole, Tebuconazole, Prothioconazole, Cyproconazole, Propiconazole and Epoxiconazole wherein component (A) and component (B) are present in said composition in amounts which produce a synergistic effect.

In a particular embodiment of the invention said composition comprises as plant growth regulating and/or fungicidal active ingredient a mixture of (A) Paclobutrazole and (B) Difenoconazole wherein said (A) and (B) are present in said composition in amounts which produce a synergistic effect. In a preferred embodiment said composition comprises as plant growth regulating active ingredient a mixture of Paclobutrazole and Difenoconazole in amounts which produce a synergistic effect. In a still further embodiment of the invention component (A) is Paclobutrazole in the free form.

In a still further embodiment said composition comprises as plant growth regulating and/or fungicidal active ingredient a mixture of (A) Paclobutrazole and (B) Metconazole wherein said (A) and (B) are present in said composition in amounts which produce a synergistic effect.

In a still further embodiment said composition comprises as plant growth regulating and/or fungicidal active ingredient a mixture of (A) Paclobutrazole and (B) Ipconazole wherein said (A) and (B) are present in said composition in amounts which produce a synergistic effect.

In a still further embodiment said composition comprises as plant growth regulating and/or fungicidal active ingredient a mixture of (A) Paclobutrazole and (B) Tebuconazole wherein said (A) and (B) are present in said composition in amounts which produce a synergistic effect.

In a still further embodiment said composition comprises as plant growth regulating and/or fungicidal active ingredient a mixture of (A) Paclobutrazole and (B) Prothioconazole wherein said (A) and (B) are present in said composition in amounts which produce a synergistic effect.

In a still further embodiment said composition comprises as plant growth regulating and/or fungicidal active ingredient a mixture of (A) Paclobutrazole and (B) Cyproconazole wherein said (A) and (B) are present in said composition in amounts which produce a synergistic effect.

In a still further embodiment said composition comprises as plant growth regulating and/or fungicidal active ingredient a mixture of (A) Paclobutrazole and (B) Propiconazole wherein said (A) and (B) are present in said composition in amounts which produce a synergistic effect.

In a still further embodiment said composition comprises as plant growth regulating and/or fungicidal active ingredient a mixture of (A) Paclobutrazole and (B) Epoxiconazole wherein said (A) and (B) are present in said composition in amounts which produce a synergistic effect.

The present invention still further provides a composition capable of regulating growth of a plant or propagation material thereof and/or controlling phytopathogenic fungi on a plant or propagation material thereof comprising as growth regulating and/or fungicidal active ingredient a mixture of component (A) and component (B) wherein component (A) is Prohexadione and component (B) is selected from the group consisting of Difenoconazole, Ipconazole, Metconazole, Tebuconazole, Prothioconazole, Cyproconazole, Propiconazole and Epoxiconazole wherein component (A) and component (B) are present in said composition in amounts which produce a synergistic effect. In a particular embodiment said composition comprises as plant growth regulating active ingredient a mixture of Prohexadione and Metconazole in amounts which produce a synergistic effect. In a still further embodiment of the invention said Prohexadione is used as a calcium salt.

The present invention still further provides a composition capable of regulating growth of a plant or propagation material thereof and or controlling phytopathogenic fungi on a plant or propagation material thereof comprising as growth regulating and/or fungicidal active ingredient a mixture of component (A) and component (B) wherein component (A) is Chlormequat and component (B) is selected from the group consisting of Difenoconazole, Ipconazole, Prothioconazole, Cyproconazole, Propiconazole and Epoxiconazole wherein component (A) and component (B) are present in said composition in amounts which produce a synergistic effect. In a still further embodiment of the invention Chlormequat is used as a chloride salt.

In a still further embodiment of the invention component (B) is used in the free form.

The compositions according to the invention have, inter alia, pronounced growth-regulating properties, which can result in an increase in the yield and quality of cultivated plants and/or harvested crops.

The compositions according to the invention are capable of inhibiting the vegetative growth of both monocots and dicots. Inhibition of the vegetative growth of cultivated plants permits more plants to be sown in a crop area, so that a higher yield may be obtained per unit of area. A further mechanism of yield increase using growth regulators resides in the fact that nutrients are able to promote flower formation and fruiting to a greater extent, whilst vegetative growth is inhibited.

Inhibition of the vegetative growth of monocot plants, e.g. grasses or also cultivated plants such as cereals, is sometimes desirable and advantageous. Such a growth inhibition is of economic interest, inter alia, in respect of grasses, as the frequency of cutting in flower gardens, parks, sport fields or road shoulders can thereby reduced. It is also desirable to inhibit growth of herbaceous and ligneous plants on road shoulders and near transmission lines, or generally in areas in which strong growth is unwanted.

The use of growth regulators for inhibiting the growth in height of cereals and oilseed rape is also important, as shortening the stalks diminishes or completely eliminates the danger of lodging before harvesting. In addition, growth regulators are able to bring about a strengthening of the stalks in crops of cereals and this too counteracts lodging.

However, besides the actual surprising synergistic action with respect to regulating plant growth, the compositions according to the invention can also have further surprising advantageous properties which can also be described, in a wider sense, as synergistic activity.

Examples of such advantageous properties that may be mentioned are: a synergistic fungicidal activity, e.g. the rates of application of the triazole fungicide and the growth regulator are lowered whilst the fungicidal action remains equally good; a broadening of the spectrum of fungicidal activity to other phytopathogens, for example to resistant strains; a reduction in the rate of application of the active ingredients; more advantageous degradability; improved toxicological and/or ecotoxicological behaviour.

Components (A) and components (B) are described in "The Pesticide Manual" [The Pesticide Manual—A World Compendium; Thirteenth Edition; Editor: C. D. S. Tomlin; The British Crop Protection Council]. Paclobutrazole is described therein under the entry number 612, Prohexadione under entry number 664, Chlormequat under entry number 137, Difenoconazole under entry number 247, Ipconazole under entry number 468, Metconazole under entry number 525, Tebuconazole under entry number 761, Prothioconazole under entry number 685, Cyproconazole under entry number 207, Propiconazole under entry number 675 and Epoxiconazole is described under entry number 298.

Components (A) and components (B) can exist in different stereoisomeric forms. The invention covers mixtures comprising all those stereoisomeric forms or mixtures of those stereoisomeric forms in any ratio.

Accordingly, the present invention provides that Paclobutrazole, Difenoconazole, Ipconazole, Metconazole, Tebuconazole, Prothioconazole, Cyproconazole, Propiconazole and Epoxiconazole can be used either in their free form or as a salts or metal complexes thereof.

The mentioned salts of Paclobutrazole and/or Difenoconazole can be prepared by reacting the respective free form of Paclobutrazole and/or Difenoconazole with acids.

Of the acids that can be used for the preparation of salts of Paclobutrazole and/or Difenoconazole, the following may be mentioned: hydrohalic acids, such as hydrofluoric acid, hydrochloric acid, hydrobromic acid or hydriodic acid; sulfuric acid, phosphoric acid, nitric acid, and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid and 1,2-naphthalene-disulfonic acid. Metal complexes consist of the underlying organic molecule and an inorganic or organic metal salt, for example a halide, nitrate, sulfate, phosphate, acetate, trifluoroacetate, trichloroacetate, propionate, tartrate, sulfonate, salicylate, benzoate, etc., of an element of main group II, such as calcium and magnesium, and of main groups III and IV, such as aluminium, tin or lead, and of subgroups I to VIII, such as chromium, manganese, iron, cobalt, nickel, copper, zinc, etc. Preference is given to the subgroup elements of the 4th period. The metals may have any of the different valencies in which they occur. The metal complexes can be mono- or poly-nuclear, i.e. they can contain one or more organic molecule components as ligands.

The present invention still further provides a composition as described above wherein said composition regulates plant growth by inhibiting growth of the plant or propagation material thereof.

Throughout this specification the expression "composition" stands for the various mixtures or combinations of component (A) and component (B), for example in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying component (A) and component (B) is not essential for working the present invention.

The compositions according to the invention may also comprise additional pesticides.

The compositions according to the invention are effective against harmful microorganisms, such as microorganisms, that cause phytopathogenic diseases, in particular against phytopathogenic fungi and bacteria.

The compositions according to the invention are effective especially against phytopathogenic fungi belonging to the following classes: Ascomycetes (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago* (such as *Ustilago nuda*), *Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*). Throughout this specification the term "plant"/"plants" includes plants of the following species: grape vines; cereals, such as wheat, barley, rye or oats; beet, such as sugar beet or fodder beet; fruits, such as pomes, stone fruits or soft fruits, for example apples, pears, plums, peaches, almonds, cherries, strawberries, raspberries or blackberries; leguminous plants, such as beans, lentils, peas or soybeans; oil plants, such as rape, mustard, poppy, olives, sunflowers, coconut, castor oil plants, cocoa beans or groundnuts; cucumber plants, such as marrows, cucumbers or melons; fibre plants, such as cotton, flax, hemp or jute; citrus fruit, such as oranges, lemons, grapefruit or mandarins; vegetables, such as spinach, lettuce, asparagus, cabbages, carrots, onions, tomatoes, potatoes, cucurbits or paprika; lauraceae, such as avocados, cinnamon or camphor; maize; tobacco; nuts; coffee; sugar cane; tea; vines; hops; durian; bananas; natural rubber plants; turf or ornamentals, such as flowers, shrubs, broad-leaved trees or evergreens, for example conifers.

More specifically, "plant"/"plants" of particular interest in connection with present invention are cereals; soybean; rice; oil seed rape; pome fruits; stone fruits; peanuts; coffee; tea; strawberries; turf; vines and vegetables, such as tomatoes, potatoes, cucurbits and lettuce.

The term "plant"/"plants" also includes genetically modified plants including those plants which have been rendered resistant to herbicides, insecticides, fungicides or have been modified in some other way such as to enhance yield, drought tolerance or quality. Such genetically modified plants may have been modified via recombinant nucleic acid techniques well know to the person skilled in the art.

The term "locus" of a plant as used herein is intended to embrace the place on which the plants are growing, where the plant propagation materials of the plants are sown or where the plant propagation materials of the plants will be placed into the soil. An example for such a locus is a field, on which crop plants are growing.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion.

In a particular embodiment "plant propagation material" means seeds.

The compositions according to the invention are particularly effective against powdery mildews; rusts; leafspot species; early blights and molds; especially against *Septoria, Puccinia, Erysiphe, Pyrenophora, Fusarium* and/or *Tapesia* in cereals; *Phakopsora* in soybeans; *Hemileia* in coffee; *Phragmidium* in roses; *Alternaria* in potatoes, tomatoes and cucurbits; *Sclerotinia* in turf, vegetables, sunflower and oil seed rape; black rot, red fire, powdery mildew, grey mold and dead arm disease in vine; *Botrytis cinerea* in fruits; *Monilinia* spp. in fruits.

The compositions according to the invention are particularly useful for controlling the following plant diseases:
*Alternaria* species in fruit and vegetables,
*Ascochyta* species in pulse crops,
*Botrytis cinerea* in strawberries, tomatoes, sunflower, pulse crops, vegetables and grapes,
*Cercospora arachidicola* in peanuts,
*Cochliobolus sativus* in cereals,
*Colletotrichum* species in pulse crops,
*Erysiphe* species in cereals,
*Erysiphe cichoracearum* and *Sphaerotheca fuliginea* in cucurbits,
*Fusarium* species in cereals and maize,
*Gäumannomyces graminis* in cereals and lawns,
*Helminthosporium* species in maize, rice and potatoes,
*Hemileia vastatrix* on coffee,
*Microdochium* species in wheat and rye,
*Phakopsora* species in soybean,
*Puccinia* species in cereals, broadleaf crops and perennial plants,
*Pseudocercosporella* species in cereals,
*Phragmidium mucronatum* in roses,
*Podosphaera* species in fruits,
*Pyrenophora* species in barley,
*Pyricularia oryzae* in rice,
*Ramularia collo-cygni* in barley,
*Rhizoctonia* species in cotton, soybean, cereals, maize, potatoes, rice and lawns,
*Rhynchosporium secalis* in barley and rye,
*Sclerotinia* species in lawns, lettuce, vegetables and oil seed rape,
*Septoria* species in cereals, soybean and vegetables,
*Sphacelotheca reilliana* in maize,
*Tilletia* species in cereals,
*Uncinula necator, Guignardia bidwellii* and *Phomopsis viticola* in vines,
*Urocystis occulta* in rye,
*Ustilago* species (such as *Ustilago nuda*) in cereals and maize,
*Venturia* species in fruits,
*Monilinia* species on fruits,
*Mycosphaerella fijiensis* on banana.

The compositions according to the invention have a systemic fungicidal action and can be used as foliar, soil and seed treatment fungicides.

Via use of the compositions according to the invention, it is possible to inhibit or destroy the phytopathogenic microorganisms which occur in plants or in parts of plants (fruit, blossoms, leaves, stems, tubers, roots) in different useful plants, while at the same time the parts of plants which grow later are also protected from attack by phytopathogenic microorganisms.

The compositions according to the invention are of particular interest for controlling a large number of fungi in various useful plants or their seeds, especially in grape vines; cereals, such as wheat, barley, rye or oats; beet, such as sugar beet or fodder beet; fruits, such as pomes, stone fruits; leguminous plants, such as beans, lentils, peas or soybeans; oil plants, such as rape, mustard, poppy, olives, sunflowers; fibre plants, such as cotton; vegetables, such as lettuce, cabbages, tomatoes, potatoes; lauraceae, such as avocados; coffee; bananas; turf or ornamentals.

The compositions according to the invention can be applied by treating the fungi, the plants, the locus thereof or the propagation material thereof with a composition according to the invention. The application may be made to the soil before emergence of the plants, either pre-planting or post-planting. The application may be made as a foliar spray at different timings during crop development, with either one or two applications early or late post-emergence.

The compositions according to the invention can be applied before or after infection of the useful plants or the propagation material thereof by the fungi.

The amount of a composition according to the invention to be applied, will depend on various factors, such as the subject of the treatment, such as, for example plants, soil or seeds; the type of treatment, such as, for example spraying, dusting or seed dressing; the purpose of the treatment, such as, for example prophylactic or therapeutic disease control; in case of disease control the type of fungi to be controlled or the application time.

The weight ratio of component (A) to component (B) is so selected as one which provides a synergistic activity. In general the weight ratio of component (A) to component (B) is from 1000:1 to 1:1000, preferably from 100:1 to 1:100, more preferably from 10:1 to 1:10, more preferably from 6:1 to 1:6, for example Paclobutrazole: Difenoconazole equals 1:2.

The synergistic activity of the compositions according to the invention is apparent from the fact that the growth regulating property of the composition of component (A) and component (B) is greater than the sum of the growth regulating properties of component (A) and component (B).

When applied to plants component (A) is applied at a rate of 5 to 2000 g a.i./ha, particularly 10 to 1000 g a.i./ha, e.g. 37.5, 50, 62.5, 75, 100 or 200 g a.i./ha, in association with 1 to 5000 g a.i./ha, particularly 2 to 2000 g a.i./ha, e.g. 75, 100, 125, 250, 500, 800, 1000, 1500 g a.i./ha of component (B).

In agricultural practice the application rates of the compositions according to the invention depend on the type of effect desired, and typically range from 20 to 4000 g of total composition per hectare, preferably 20 to 1000 g of total composition per hectare.

When the compositions according to the invention are used for treating seed, rates of 0.001 to 50 g of component (A) per kg of seed, preferably from 0.01 to 10 g per kg of seed, and 0.001 to 50 g of component (B), per kg of seed, preferably from 0.01 to 10 g per kg of seed, are generally sufficient.

The composition of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate inert formulation adjuvants (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least component (A) together with component (B), and optionally other active agents, particularly microbiocides or conservatives or the like, Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

The present invention still further provides a method of regulating growth of a plant or propagation material thereof comprising applying to the plant, the locus thereof or propagation material thereof a composition as described above. In a particular embodiment of the invention the composition comprises as plant growth regulating active ingredient a mixture of Paclobutrazole and Difenoconazole in amounts which produce a synergistic effect.

The present invention still further provides a method of regulating growth of a plant to obtain an increase in yield, comprising applying to the plant, the locus thereof or propagation material thereof a composition as described above. Preferably the composition comprises as plant growth regulating active ingredient a mixture of Paclobutrazole and Difenoconazole in amounts which produce a synergistic effect.

The present invention still further provides a method of controlling phytopathogenic disease on a plant or on propagation material thereof, comprising applying to the plant, the locus thereof or propagation material thereof a composition as described above. In a particular embodiment the composition is applied to the plant or to the locus thereof. In a still further embodiment the composition is applied to the propagation material of the plant.

The present invention still further provides a method as described above wherein the plant or propagation material is a cereal or oil seed rape plant or propagation material.

In a further aspect of the invention there is provided the use of a composition as described above in a method of regulating the growth of a plant or propagation material thereof. In a particular embodiment of the invention growth of said plant or said propagation material is inhibited. In a further embodiment of the invention said plant or said propagation material is a cereal or oil seed rape plant or propagation material.

In a still further aspect there is provided the use of a composition as described above in the prevention and/or treatment of growth and/or infestation of phytopathogenic fungi on a plant or propagation material thereof. In a further embodiment of the invention said plant or said propagation material is a cereal or oil seed rape plant or propagation material.

The Examples which follow serve to illustrate the invention, "active ingredient" denoting a mixture of Component (A) and Component (B) in a specific mixing ratio.

FORMULATION EXAMPLES

| Wettable powders | (a) | (b) |
| --- | --- | --- |
| active ingredient A):B) = 1:3(a), 1:2(b) | 25% | 50% |
| sodium lignosulfonate | 5% | 5% |
| sodium lauryl sulfate | 3% | — |
| sodium diisobutylnaphthalenesulfonate | — | 6% |
| phenol polyethylene glycol ether (7-8 mol of ethylene oxide) | — | 2% |

| Wettable powders | (a) | (b) |
|---|---|---|
| highly dispersed silicic acid | 5% | 10% |
| Kaolin | 62% | 27% |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) |
|---|---|---|
| active ingredient A):B) = 1:3(a), 1:2(b) | 25% | 50% |
| light mineral oil | 5% | 5% |
| highly dispersed silicic acid | 5% | 5% |
| Kaolin | 65% | 40% |
| Talcum | — | — |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient (A):B) = 1:6) | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) |
|---|---|---|
| Active ingredient A):B) = 1:6(a), 1:2(b) | 5% | 6% |
| Talcum | 95% | — |
| Kaolin | — | 94% |
| mineral filler | — | — |

Ready-for-use dusts are obtained by mixing the active ingredient with the carrier and grinding the mixture in a suitable mill. Such powders can also be used for dry dressings for seed.

| Extruder granules | |
|---|---|
| Active ingredient (A):B) = 2:1) | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient (A):B) = 1:10) | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Suspension concentrate | |
|---|---|
| active ingredient (A):B) = 1:8) | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient (A):B) = 1:8) | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of a compound of component (A) and a compound of component (B), or of each of these compounds separately, are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

BIOLOGICAL EXAMPLES

A synergistic effect exists whenever the action of an active ingredient combination, such as, for example, the plant growth regulating property or the fungicidal activity, is greater than the sum of the actions of the individual components.

The action to be expected E for a given active ingredient combination obeys the so-called COLBY formula and can be calculated as follows (COLBY, S. R. "Calculating synergistic and antagonistic responses of herbicide combination". Weeds, Vol. 15, pages 20-22; 1967):

X=% action by active ingredient A) at a given certain amount of active ingredient Y=% action by active ingredient B) at a given certain amount of active ingredient.

According to COLBY, the expected combined action of active ingredients A)+B) is:

$$E = X + Y - \frac{X \cdot Y}{100}$$

If the activity actually observed (O) is greater than the expected combined action (E), then the activity of the combination is super-additive, i.e. there is a synergistic effect. In mathematical terms the synergism factor SF corresponds to the quotient of O/E.

Example B-1

Plant Growth Regulation ("PGR"): Pre-Emergence

The compounds are sprayed with a vertical boom sprayer at the mentioned rates (ref. result-tables) pre-plant on the bare soil, then they are incorporated into the soil and the plants are seeded. After 14 days the plant growth is evaluated vs. an untreated control.

PGR of Barley
Dosage in mg active ingredient/liter final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 12.5 | — | — | 0 | — |
| 25 | — | — | 10 | — |
| 50 | — | — | 30 | — |
| — | 25 | — | 0 | — |
| — | 50 | — | 0 | — |
| — | 100 | — | 0 | — |
| 12.5 | 25 | 0 | 10 | >100 |
| 25 | 50 | 10 | 25 | 2.50 |
| 50 | 100 | 30 | 38 | 1.27 |

PGR of Oat
Dosage in mg active ingredient/litre final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 25 | — | — | 30 | — |
| 50 | — | — | 40 | — |
| — | 50 | — | 0 | — |
| — | 100 | — | 0 | — |
| 25 | 50 | 30 | 35 | 1.17 |
| 50 | 100 | 40 | 45 | 1.13 |

PGR of Oilseed Rape
Dosage in mg active ingredient/liter final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 12.5 | — | — | 40 | — |
| 25 | — | — | 50 | — |
| 50 | — | — | 55 | — |
| — | 25 | — | 0 | — |
| — | 50 | — | 0 | — |
| — | 100 | — | 0 | — |
| 12.5 | 25 | 40 | 45 | 1.13 |
| 25 | 50 | 50 | 55 | 1.10 |
| 50 | 100 | 55 | 60 | 1.09 |

PGR of Soybean
Dosage in mg active ingredient/liter final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 25 | — | — | 30 | — |
| 50 | — | — | 50 | — |
| — | 50 | — | 0 | — |
| — | 100 | — | 0 | — |
| 25 | 50 | 30 | 45 | 1.50 |
| 50 | 100 | 50 | 60 | 1.20 |

PGR of Triticale
Dosage in mg active ingredient/liter final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 25 | — | — | 10 | — |
| 50 | — | — | 30 | — |
| — | 50 | — | 0 | — |
| — | 100 | — | 0 | — |
| 25 | 50 | 10 | 25 | 2.50 |
| 50 | 100 | 30 | 45 | 1.50 |

PGR of Wheat
Dosage in mg active ingredient/liter final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 12.5 | — | — | 20 | — |
| 25 | — | — | 25 | — |
| 50 | — | — | 40 | — |
| — | 25 | — | 0 | — |
| — | 50 | — | 0 | — |
| — | 100 | — | 0 | — |
| 12.5 | 25 | 20 | 25 | 1.25 |
| 25 | 50 | 25 | 30 | 1.20 |
| 50 | 100 | 40 | 45 | 1.13 |

PGR of Rye
Dosage in mg active ingredient/liter final medium

| Paclo-butrazole [mg/L] | Difeno-conazole [mg/L] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| 25 | — | — | 25 | — |
| 50 | — | — | 40 | — |
| — | 50 | — | 0 | — |
| — | 100 | — | 0 | — |
| 25 | 50 | 25 | 35 | 1.40 |
| 50 | 100 | 40 | 50 | 1.25 |

Example B-2

Plant Growth Regulation ("PGR"); Post-Emergence

The plants are seeded and grown in a greenhouse until Growth Stage 12 (2 leafs unfolded). Then the compounds/mixture of the compounds are sprayed with a vertical boom sprayer top over the leafs. The plant growth is evaluated vs. an untreated control, 14 days after application.

PGR of summer and winter rape

| Paclo-butrazole [g a.i./ha] | Difeno-conazole [g a.i./ha] | Expected PGR in % (% $C_{exp}$) expected | Observed PGR in % (% $C_{obs}$) observed | Synergy Factor SF % $C_{obs}$/% $C_{exp}$ Factor |
|---|---|---|---|---|
| Summer rape "Hybridol" | | | | |
| 31.3 | — | — | 17 | — |
| 62.5 | — | — | 23 | — |
| — | 62.5 | — | 0 | — |
| — | 125 | — | 0 | — |
| 31.3 | 62.5 | 17 | 27 | 1.1 |
| 62.5 | 125 | 23 | 27 | 1.6 |
| Winter rape "Colza d'hiver Aviso" | | | | |
| 31.3 | — | — | 30 | — |
| 62.5 | — | — | 33 | — |
| — | 62.5 | — | 0 | — |
| — | 125 | — | 0 | — |
| 31.3 | 62.5 | 30 | 40 | 1.3 |
| 62.5 | 125 | 33 | 47 | 1.4 |

Example C-1

Fungicidal Action Against *Botrytis cinerea*—Fungal Growth Assay

Conidia of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 48-72 hrs.

Example C-2

Fungicidal Action Against *Septoria tritici* on Wheat a) Fungal Growth Assay
Conidia of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 72 hrs.
b) Protective Treatment
2 week old wheat plants cv. Riband are treated with the formulated test compound (0.2% active ingredient) in a spray chamber. One day after application, wheat plants are inoculated by spraying a spore suspension ($10 \times 10^5$ conidia/ml) on the test plants. After an incubation period of 1 day at 23° C. and 95% relative humidity, the plants are kept for 16 days at 23° C. and 60% relative humidity in a greenhouse. The disease incidence is assessed 18 days after inoculation.

Example C-3

Fungicidal Action Against Pyricularia Oryzae on Rice a) Fungal Growth Assay
Conidia of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 72 hrs.
b) Protective Treatment
Rice leaf segments are placed on agar in multi well plates (24-well format) and sprayed with test solutions. After drying, the leaf disks are inoculated with a spore suspension of the fungus. After appropriate incubation the activity of a compound is assessed 96 hrs after inoculation as preventive fungicidal activity.

Example C-4

Fungicidal Action Against *Alternaria* spp.

a) Fungal Growth Assay
a1) *Alternaria solani* (Early Blight)
Conidia—harvested from a freshly grown colony—of the fungus are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 48 hrs.

a2) *Alternaria brassicae* (Black Spot of Rape):

Conidia—harvested from a freshly grown colony—of the fungus are directly mixed into nutrient broth (PDB potato dextrose broth). After placing a (DMSO) solution of the test compounds into a micro titer plate (96-well format) the nutrient broth containing the fungal spores is added. The test plates are incubated at 24 C and the inhibition of growth is determined photometrically after 72 hrs.

a3) *Alternaria brassicicola* (Silique Mould of Rape):

Conidia—harvested from a freshly grown colony—of the fungus are directly mixed into nutrient broth (PDB potato dextrose broth). After placing a (DMSO) solution of the test compounds into a micro titer plate (96-well format) the nutrient broth containing the fungal spores is added. The test plates are incubated at 24 C and the inhibition of growth is determined photometrically after 48 hrs.

b) Protective Treatment

*Alternaria solani* (Early Blight)

4 week old tomato plants cv. Roter Gnom are treated with the formulated test compound (0.02% active ingredient) in a spray chamber. Two days after application, the tomato plants are inoculated by spraying a spore suspension ($2\times10^5$ conidia/ml) on the test plants. After an incubation period of 3 days at 20° C. and 95% relative humidity in a growth chamber the disease incidence is assessed.

Example C-5

Fungicidal Action Against *Pyrenopeziza brassicae* (syn. *Cylindrosporium concentricum*, Light Leaf Spot of Rape)—Fungal Growth Assay Conidia—harvested from a freshly grown colony—of the fungus are directly mixed into nutrient broth (PDB potato dextrose broth). After placing a (DMSO) solution of the test compounds into a micro titer plate (96-well format) the nutrient broth containing the fungal spores is added. The test plates are incubated at 24 C and the inhibition of growth is determined photometrically after 48 hrs.

Example C-6

Fungicidal Action Against *Venturia inaequalis* on Apple a) Fungal Growth Assay

Conidia of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 144 hrs.

b) Protective Treatment 4 week old apple seedlings cv. McIntosh are treated with the formulated test compound (0.02% active ingredient) in a spray chamber. One day after application, the apple plants are inoculated by spraying a spore suspension ($4\times10^5$ conidia/ml) on the test plants. After an incubation period of 4 days at 21° C. and 95% relative humidity the plants are placed for 4 days at 21° C. and 60% relative humidity in a greenhouse. After another 4 day incubation period at 21° C. and 95% relative humidity the disease incidence is assessed.

Example C-7

Fungicidal Action Against *Pythium ultimum* (Damping Off)—Fungal Growth Assay

Mycelial fragments of the fungus, prepared from a fresh liquid culture, are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 48 hrs.

Example C-8

Fungicidal Action Against *Leptosphaeria* spp.—Fungal Growth Assay a1) *Leptosphaeria nodorum* (Glume Blotch):

Conidia of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 48 hrs.

a2) *Leptosphaeria maculans* (syn. *Phoma lingam*, Black Leg of Crucifers):

Conidia—harvested from a freshly grown colony—of the fungus are directly mixed into nutrient broth (PDB potato dextrose broth). After placing a (DMSO) solution of the test compounds into a micro titer plate (96-well format) the nutrient broth containing the fungal spores is added. The test plates are incubated at 24 C and the inhibition of growth is determined photometrically after 48 hrs.

Example C-9

Fungicidal Action Against *Pseudocercosporella herpotrichoides* Var. *acuformis* (Eyespot/Cereals)—Fungal Growth Assay Conidia of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 72 hrs.

Example C-10

Fungicidal Action Against *Puccinia recondita* (Brown Rust) on Wheat a) Protective Treatment of Leaf Segments Wheat leaf segments are placed on agar in multi well plates (24-well format) and sprayed with test solutions. After drying, the leaf disks are inoculated with a spore suspension of the fungus. After appropriate incubation the activity of a compound is assessed 9 days after inoculation as preventive fungicidal activity.

b) Protective Treatment of Plants 1 week old wheat plants cv. Arina are treated with the formulated test compound (0.02% active ingredient) in a spray chamber. One day after application, the wheat plants are inoculated by spraying a spore suspension ($1\times10^5$ uredospores/ml) on the test plants. After an incubation period of 2 days at 20° C. and 95% relative humidity the plants are kept in a greenhouse for 8 days at 20° C. and 60% relative humidity. The disease incidence is assessed 10 days after inoculation.

Example C-11

Fungicidal Action Against *Septoria nodorum* on Wheat a) Protective Treatment of Leaf Segments Wheat leaf segments are placed on agar in multi well plates (24-well format) and sprayed with test solutions. After drying, the leaf disks are inoculated with a spore suspension of the fungus. After appropriate incubation the activity of a compound is assessed 96 hrs after inoculation as preventive fungicidal activity.

b) Protective Treatment of Plants 1 week old wheat plants cv. Arina are treated with the formulated test compound (0.02% active ingredient) in a spray chamber. One day after application, the wheat plants are inoculated by spraying a spore suspension ($5 \times 10^5$ conidia/ml) on the test plants. After an incubation period of 1 day at 20° C. and 95% relative humidity the plants are kept for 10 days at 20° C. and 60% relative humidity in a greenhouse. The disease incidence is assessed 11 days after inoculation.

Example C-12

Fungicidal Action Against *Uncinula necator* (Powdery Mildew) on Grapes—Protective Treatment 5 week old grape seedlings cv. Gutedel are treated with the formulated test compound (0.02% active ingredient) in a spray chamber. One day after application, the grape plants are inoculated by shaking plants infected with grape powdery mildew above the test plants. After an incubation period of 7 days at 26° C. and 60% relative humidity under a light regime of 14/10 hours (light/dark) the disease incidence is assessed.

Example C-13

Fungicidal Action Against *Scierotinia scierotiorum* (Cottony Rot)—Fungal Growth Assay Mycelial fragments of the fungus, prepared from a fresh liquid culture, are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 48 hrs.

Example C-14

Fungicidal Action Against *Rhizoctonia solani* (Foot Rot Damping-Off)—Fungal Growth Assay Mycelial fragments of the fungus from cryogenic storage are directly mixed into nutrient broth (PDB potato dextrose broth). After placing a (DMSO) solution of the test compounds into a micro titer plate (96-well format) the nutrient broth containing the fungal spores is added. The test plates are incubated at 24° C. and the inhibition of growth is determined photometrically after 48 hrs.

Example C-15

Fungicidal Action Against *Phakopsora pachyrhizi* (Soybean Rust on Soybean)—Protective Treatment Treatment of the soybean leaves with the recited active ingredients are conducted 4 weeks after planting in a spray chamber, Before or after spray, leaf discs are cut from the first trifoliate leaf and placed into multi-well plates on agar. The leaf discs are then inoculated with *Phakopsora pachyrhizi* (Asian soybean rust (ASR)) one day after treatment (curative). Evaluations of the leaves are conducted ten days after inoculation.

Example C-16

Fungicidal Action Against *Puccinia recondita* (Brown Rust)—Protective Treatment Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 9 days after inoculation as preventative fungicidal activity.

The compositions according to the invention exhibit good fungicidal activity in examples C-1 to C-16.

The invention claimed is:

1. A composition comprising a mixture of component (A) and component (B), wherein component (A) is Paclobutrazole and component (B) is Difenoconazole, wherein component (A) and component (B) are present in said composition in amounts which produce a synergistic plant growth regulating effect.

2. A composition according to claim 1 wherein the weight ratio of component (A) to component (B) is from 1000:1 to 1:1000.

3. A composition according to claim 1 wherein said composition regulates plant growth by inhibiting growth of the plant or propagation material thereof.

4. A method of regulating growth of a plant or propagation material thereof comprising applying to the plant, the locus thereof or propagation material thereof a composition according to claim 1.

5. A method of regulating growth of a plant to obtain an increase in yield, comprising applying to the plant, the locus thereof or propagation material thereof a composition according to claim 1.

6. A method of controlling phytopathogenic disease on a plant or on propagation material thereof, comprising applying to the plant, the locus thereof or propagation material thereof a composition according to claim 1.

7. A method according to claim 4, wherein the composition is applied to the plant or to the locus thereof.

8. A method according to claim 4, wherein the composition is applied to the propagation material of the plant.

9. A method according to claim 4 wherein the plant or propagation material is a cereal or oil seed rape plant or propagation material.

10. A composition according to claim 1 wherein said composition controls phytopathogenic fungi on a plant or propagation material thereof.

11. A method according to claim 5, wherein the composition is applied to the plant or to the locus thereof.

12. A method according to claim 5, wherein the composition is applied to the propagation material of the plant.

13. A method according to claim 5, wherein the plant or propagation material is a cereal or oil seed rape plant or propagation material.

14. A method according to claim 6, wherein the composition is applied to the plant or to the locus thereof.

15. A method according to claim 6, wherein the composition is applied to the propagation material of the plant.

16. A method according to claim 6, wherein the plant or propagation material is a cereal or oil seed rape plant or propagation material.

17. A composition according to claim 1 wherein the weight ratio of component (A) to component (B) is 1:2.

* * * * *